United States Patent [19]
Utterberg

[11] Patent Number: 5,983,947
[45] Date of Patent: Nov. 16, 1999

[54] DOCKING PORTS FOR MEDICAL FLUID SETS

[75] Inventor: David S. Utterberg, Seattle, Wash.

[73] Assignee: Medisystems Technology Corporation, Las Vegas, Nev.

[21] Appl. No.: 08/810,361

[22] Filed: Mar. 3, 1997

[51] Int. Cl.[6] .................................................. F16L 55/10
[52] U.S. Cl. .................... 138/89; 138/96 R; 138/106; 138/109
[58] Field of Search .................................. 138/967, 96 R, 138/89, 106, 109; 604/190, 283, 905

[56] References Cited

U.S. PATENT DOCUMENTS

| | | | |
|---|---|---|---|
| 3,095,062 | 6/1963 | Neely | 138/109 |
| 3,412,760 | 11/1968 | Franck | 138/96 R |
| 3,976,311 | 8/1976 | Spendlove | 138/89 |
| 4,617,012 | 10/1986 | Vaillancourt | 604/283 |
| 4,867,739 | 9/1989 | Kawano | 604/905 |
| 5,250,040 | 10/1993 | Parks et al. | 604/283 |
| 5,385,372 | 1/1995 | Utterberg . | |

*Primary Examiner*—James F. Hook
*Attorney, Agent, or Firm*—Gerstman, Ellis & McMillin, Ltd.

[57] ABSTRACT

A medical fluid set comprises tubing sections interconnected with at least one tubing connector component which connects the tubing sections together to form the set. The set further comprises external connectors carried on ends of at least some tubing sections of the set. At least one of the tubing connector components or external connectors carry, as an integral part thereof, a retaining-sealing member for removable, sealing connection with at least one of the external connectors. The retaining-sealing member is free of fluid flow connection with the set flow path. Thus, separate or tethered closure caps for external connectors can be dispensed with.

28 Claims, 2 Drawing Sheets

DOCKING PORTS FOR MEDICAL FLUID SETS

BACKGROUND OF THE INVENTION

Medical fluid sets comprise arrays of tubing which are connected together with at least one tube connector component, to connect the various tubing sections of the set together to form the set. Some medical fluid sets, particularly sets for the extracorporeal treatment of blood [such as for hemodialysis], can be rather complex, having an array of branch tubings extending off from the main tubing pathway, one or more bubble trap chambers, and often a connected segment of larger diameter pump tubing for installation in a roller pump.

The ends of the sets carry connectors, typically luer lock connectors which have a removable closure to preserve sterility inside the set. Also, each of the branch tubings are typically terminated with a connector and a removable cap to protect set sterility prior to use, to seal the tubing from leaking, and/or to cover the luer opening of the typical connector after use. Also, some prior art teaches cap that are vented to provide tortuous path protection for tubing sets that must be gas sterilized. Other prior art such as Utterberg U.S. Pat. No. 5,385,372 shows a closure cap to a tube end connector which is on a tether or a hinged arm that connects the cap with the connector. Also, caps may be threaded to better mate with luer lock connectors and/or having a male luer member to friction fit with a female luer socket.

Because many sets, particularly hemodialysis tube sets, have many branching tubes, there is a significant cost in providing all of the connectors with caps. Additionally, separate caps can be lost or fall on the floor, which can cause a safety hazard. Additionally caps are subject to touch contamination in other ways, particularly as one hand must be devoted to each of a cap and a set connector, as the two are brought together for closing of the typical cap on the end of the connector.

By this invention, the number of separate caps which must be provided to a medical fluid set is reduced, or eliminated if desired, while the respective connectors are still provided with a means for closing and sealing prior to use of the set. Opening of the connectors may be provided by separation from a retaining, sealing member carried by the set.

DESCRIPTION OF THE INVENTION

This can be accomplished by placing a structure onto the tube set that is of the proper functional shape of a cap or protector for a desired connector. This can be done by simply molding the cap or protector functional shape as part of another molded component of the tube set. For example, one can mold such functional cap or protector shapes onto an air trap chamber top cap of the set, or onto the pump tubing segment connectors of the set, to create "docking ports" that function as caps or protectors for connectors, particularly male or female luer connectors. Thus, connectors of the set can be connected to these typically integrally molded cap or protector shapes, which have been formed on other components of the set, connecting in the same way as a separate cap but without the need for the cap. Thus, most of the cost of the cap is saved, since cap or protector functional shapes can be added to molded set components such as tube connector components at an almost negligible unit cost when mass production is considered. Additionally, such an integrally attached or molded cap or protector functional shape (called a "docking port" herein) cannot be lost or fall to the floor during manufacture or use of the set.

The docking port described above is preferably integrally molded with any desired components on a blood handling set, for example the patient connector, a pump tubing segment connector, the dialyzer connector, an injection site, the top of an air trap chamber, or the like. Additionally, a tamper evident indicator may be provided to indicate that the connector has been once separated from the docking port, and thus sterility may have been compromised.

The respective functional shapes used for a docking port may preferably be that of the front end of a conventional male luer lock connector, a female luer lock connector, a female luer, or a male luer. Thus, all the advantages of luer connection may be achieved, without the need of separate caps for the various connectors of a medical fluid set. This can achieve both advantages of convenience of use and of cost. Also, safety is an issue, since separated caps on the floor have been known to cause people to slip and fall.

Thus, a medical fluid set having a flow path is provided by this invention. The set comprises tubing sections which are interconnected with at least one tube connector component, which connects tubing sections together to form the set. The set further comprises external connectors carried on ends of at least some tubing sections of the set, particularly the patient connector, a dialyzer connector in the case of dialysis sets, or other connectors for the branching lines.

By this invention, at least one of the tube connector components or external connectors carry, as an integral part thereof, a retaining-sealing member (docking port) for removable, sealing connection with at least one external connector. The retaining-sealing member is free of fluid flow connection with the set flow path. Thus, the external connector which is connected to the retaining-sealing member is completely sealed, without communication through the seal with the set interior, just as if it were closed by a separate end cap.

Preferably, the retaining-sealing member is carried on a tube connector component which connects the tubing sections together. Typically, the tube connector component may comprise a connector positioned between and retaining different-diameter tubing sections of the set, for example pump tubing connectors which connect ends of pump tubing to other lengths of set tubing.

For connection with female luers, the retaining-sealing member may comprise a solid cylindrical member which is preferably flexible, and which is proportioned to sealingly fit into a lumen of an external connector of the set. Thus, the external connector may be removably retained and sealed until it is desired for use.

Also, the retaining-sealing member may carry a flange which extends outwardly typically from a tube connector component (or an external connector may carry the flange if that is desired). The flange may carry a retaining-sealing member (docking port) having a closed end so as to be functional as a cap but attached to the flange. Typically, the flange may carry a luer-type connector, male or female, as the retaining-sealing member.

Also, the set of this invention may have a retaining-sealing member carried on a tube connector component which comprises a set chamber. These set chambers are typically used for providing a small reservoir of blood and for bubble trapping, being connected with two or more tubing sections of the set. As in the prior art, such chambers may be tubular, but with a top cap through which one or more of the set tubings communicate to the chamber interior. By this invention, this top cap may also carry one or more retaining sealing members, either at the top or at the sides thereof. As before, the retaining-sealing member may comprise a connector having a closed end to form a docking port, particularly of the form of a male or female luer-type connector, so that connection with such a retaining-sealing member closes the external connector just like a cap, while the retaining-sealing member is integrally attached to the set chamber.

Thus, medical fluid sets may be manufactured and used with greater convenience and lower cost.

DESCRIPTION OF SPECIFIC EMBODIMENTS

Figure 1:
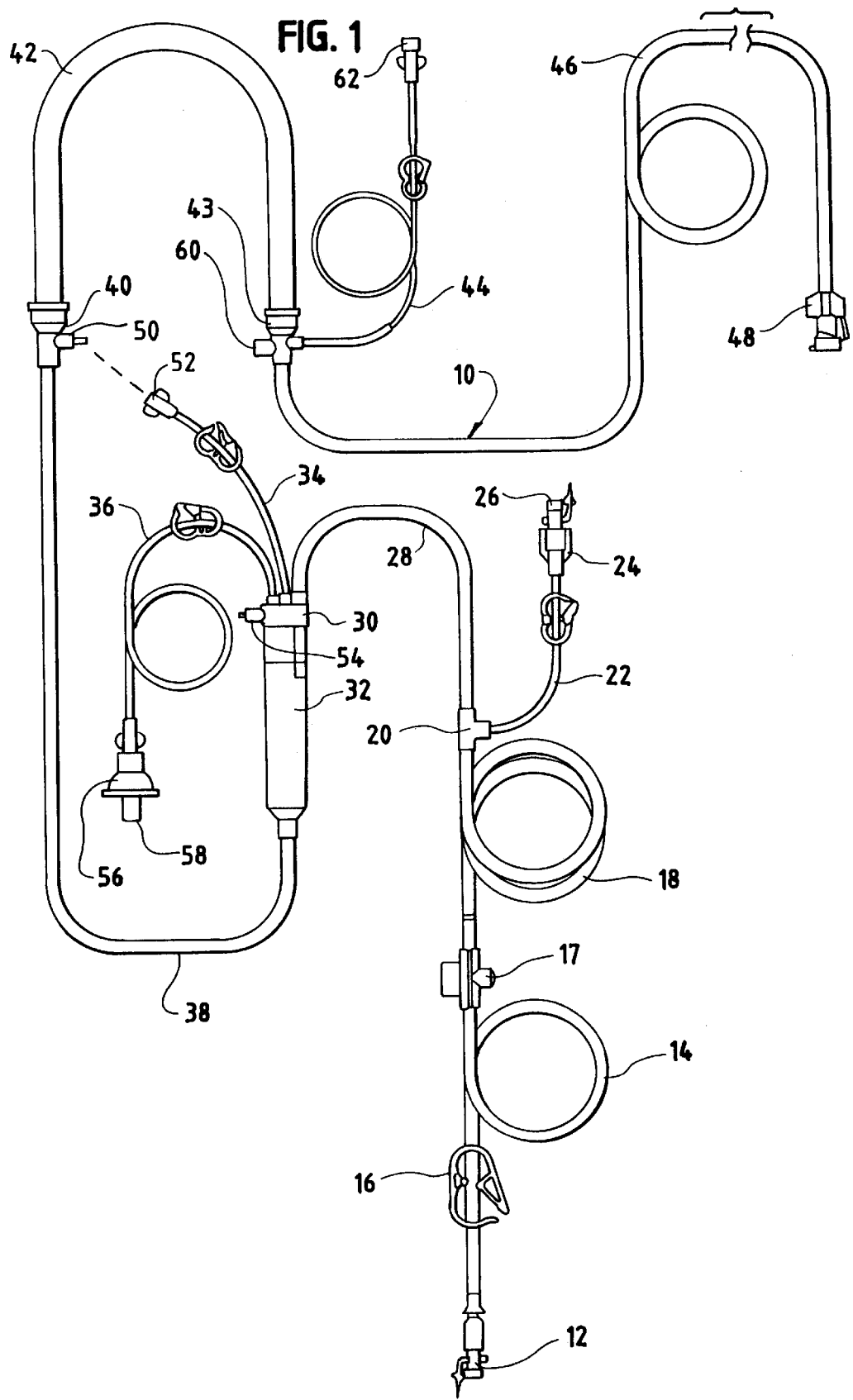
FIG. 1 is a plan view of an arterial set for hemodialysis, modified in accordance with this invention.

Referring to the drawings, an arterial set for hemodialysis is shown, which set is like a commercially available, clinically used set of the prior art, modified as described herein.

Set 10 carries a luer lock patient connector 12 which terminates a first tubing section 14 on which on/off clamp 16 resides. First tubing section 14 terminates at an injection site 17, from which extends second tubing section 18. Second tubing section 18 terminates in a T connector 20, from which a branch connector line 22 extends, terminating in a luer lock, vented recirculation connector 24 having a hinged cap 26, similar to the cap of U.S. Pat. No. 5,385,372. Third tubing section 28 extends through the top cap 30 of a tubular set chamber 32, which serves as a bubble trap. Top cap 30 also carries a pair of branch tubings 34, 36.

Fourth tubing section 38 proceeds from the bottom of chamber 32 to the first roller pump tubing connector 40. Roller pump tubing 42 extends between this first connector 40 and a second roller pump tubing connector 43 positioned at the other end thereof. Second roller pump connector 43 has a branch connection site that receives branch tubing 44.

The next, and last, section 46 of the main set tubing extends from second pump tubing connector 43, and terminates in a luer lock-type dialyzer connector 48.

Figure 3:
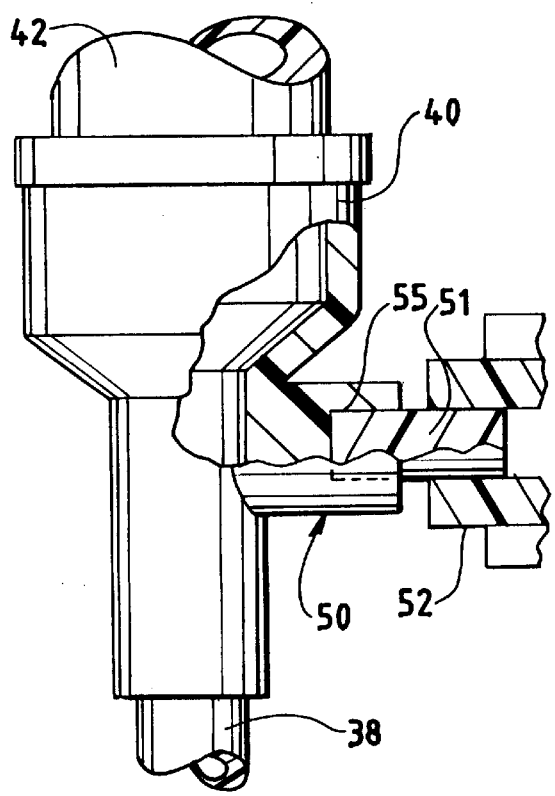
FIG. 3 is an elevational view, with a portion broken away, of a tubing connector of FIG. 1, shown connected with an external connector.

In accordance with this invention, pump tubing connector 40 carries a retaining-sealing member 50, which acts like a male connector for receiving a capless female luer connector 52 at the end of branch line 34. Retaining-sealing member 50 (FIG. 3) comprises a rod 51 of flexible elastomer or other plastic, retained and sealed in socket 55 of the molded, more rigid plastic connector 40. Rod 51 is sized to frictionally fit into the lumen of female connector 52 in a sealing, retentive manner, all as shown in FIG. 3. Thus, any cap for connector 52 is dispensed with. It simply can be pulled away from retaining-sealing member 50, and is ready for use. After use, female connector 52 may be placed again onto flexible rod 51, if desired.

A second retaining-sealing member 54 is carried on cap 30 of bubble trap chamber 32. The end of branch line 36 carries a connector with a transducer protector 56, which also has a female luer end 58. Retaining-sealing member 54 may be of the design of a male luer with an outer sleeve and an inner, tubular, frustoconical portion for sealing in the interior of a female luer, similar to reference numerals 66, 68, 84. However, the frustoconical portion may be solid rather than tubular, and it may also be of a relatively soft plastic for maximized sealing. Thus, the female luer 58 may connect with male luer shape 54, which is an integral part of cap 30, for reliable, effective sealing. Alternatively, the frustoconical portion may be replaced with a simple, properly sized, flexible, cylindrical rod for frictional retention of female luers. Particularly, the rod may be made of elastomer.

Similarly, pump tubing connector 43 may carry a male luer shape 60 in an integral manner so that the female luer connector 62 at the end of branch tubing 44 may connect therewith in sterile manner until needed.

Thus, in the specific embodiment shown in this invention, three connectors 52, 58, and 62 on the ends of branch lines may respectively be connected to separate retaining-sealing members 50, 54, 60, resulting in secure connection for the respective connectors, and with the elimination of three separate or hinged caps from the set. While it can be seen that other connectors 12, 24, 48 still carry caps in this embodiment, if desired more retaining-sealing members may be applied as integral shapes to various components of the set to eliminate the caps of these three connectors as well.

Figure 2:
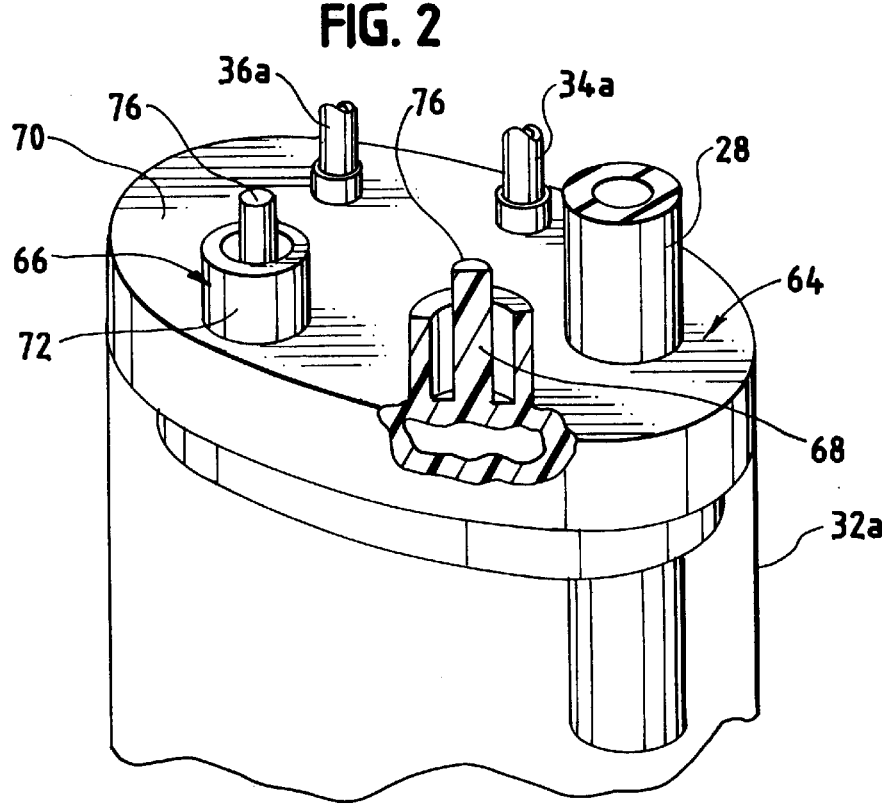
FIG. 2 is a partial, perspective view of an oval set chamber for bubble removal having docking ports on the top closure member.

Referring to FIG. 2, a substitute 32a for chamber 32 is shown, in which the cross section of the chamber 32a is oval. Tubing 38 communicates with the bottom of chamber 32a, while the inlet tubing 28 communicates with the top, extending through as shown into oval chamber 32a in a position opposed to outlet tubing 38.

Cap 64 carries conventional connections with pair of branch tubings 34a, 36a. Also, cap 64 carries a pair of male luer docking ports 66, 68, which may be used to sealingly receive female luer connectors 52, 58 of branch tubings 34, 36. Docking ports 66, 68 are an integrally molded part of cap 64, extending upwardly from top wall 70 of cap 64, with top wall 70 being intact and aperture free under the docking ports 66, 68. As can be seen, each docking port 66, 68 is in the form of the front end of a male luer connector, having an outer sleeve 72 for connection with the outer diameter of a female luer, and an inner, frustoconical, tapered member 76, which may be tubular or preferably solid, and which seals against the inner taper of the respective female luer connector.

Figure 4:
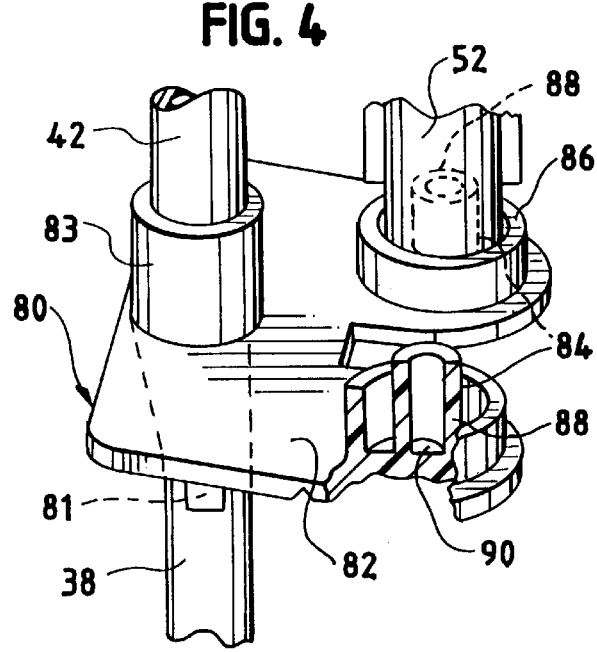
FIG. 4 is a fragmentary, perspective view of a flanged tubing connector in accordance with this invention, carrying docking ports.

Referring to FIG. 4, an alternate embodiment 80 for pump tubing connector 40 or 43 is shown.

Connector 80 comprises a connection 81 for receiving set tubing 38 and a connection 83 for pump tubing 42 in conventional, sealed tubing connection. The tubular connecting portions 81, 83 of connector 80 are of differing diameters, as needed to accommodate the respective tubings.

Also, connector 80 carries a flange 82 extending outwardly from tubes 38, 42. Flange 82 as shown carries a pair of male luer connector shapes 84, comprising the usual outer sleeve 86 for sealing the outer diameter of a female luer connector, and an inner, tapered member 88, each having a closed end 90. Each member 84 can sealingly mate with the internal luer taper of female luer connectors, for example connectors 58 and 62.

Thus, connectors on tubing sets may be sealed and retained without the need of separate closure caps.

The above has been offered for illustrative purposes only, and is not intended to limit the scope of the invention of this application, which is as defined in the claims below.

That which is claimed:

1. A medical fluid set having a flow path which comprises: tubing sections interconnected with at least one tube connector component which connects said tubing sections together to form said set, said set further comprising external connectors carried on ends of at least some tubing sections of said set, at least one of said tube connector components or external connectors carrying, as an integral part and in rigid connection therewith a retaining-sealing member for removable, sealing connection with at least one of said external connectors, said retaining-sealing member being free of fluid flow connection with the set flow path.

2. The set of claim 1 in which said retaining-sealing member is carried on said tube connector component which comprises a connector positioned between different-diameter tubing sections of the set.

3. The set of claim 1 in which said retaining-sealing member comprises a solid, cylindrical member proportioned to sealingly fit into a lumen of an external connector of said set, to removably retain and seal said external connector.

4. The set of claim 3 in which said solid, cylindrical member is flexible.

5. The set of claim 1 in which said retaining-sealing member comprises a flange extending outwardly from said tube connector component or external connector, said flange carrying a luer-type connector having a closed end.

6. The set of claim 5 in which said luer-type connector is a male luer-type connector.

7. The set of claim 1 in which said retaining-sealing member is carried on said tube connector component which comprises a set chamber.

8. The set of claim 7 in which said retaining-sealing member comprises a luer-type connector having a closed end.

9. The set of claim 8 in which said luer-type connector is a male luer-type connector.

10. The set of claim 1 in which at least one of said external connectors is in removable, sealing connection with said retaining-sealing member.

11. The set of claim 1 which is a blood set for hemodialysis.

12. The set of claim 1 in which said retaining-sealing member and said at least one tube connector component comprise an integrally molded structure.

13. The medical fluid set of claim 1 in which the retaining-sealing member is carried by a tube connector component.

14. A medical fluid set having a flow path which comprises: tubing sections interconnected with at least one tube connector component which connects said tubing sections together to form said set, said set further comprising external connectors carried on ends of at least some tubing sections of said set, at least one of said tube connector components carrying, as an integral part thereof, a retaining-sealing member which is in removable, sealing connection with at least one of said external connectors, said retaining-sealing member being free of fluid flow connection with the set flow path and comprising a flexible, substantially cylindrical member sealingly fitting into the lumen of said external connector of said set, frictionally but removably retaining and sealing said external connector.

15. The set of claim 14 in which said retaining-sealing member is carried on said tube connector component which comprises a connector positioned between different-diameter tubing sections of the set.

16. The set of claim 15 in which said retaining-sealing member and said at least one tube connector component comprise an integrally molded structure.

17. The set of claim 15 in which a flange extends outwardly from said tube connector component, said flange carrying said retaining-sealing member to receive said external connector in removable, sealed relation.

18. The set of claim 17, in which said connector carried by the flange is a luer-type connector having a closed end.

19. The set of claim 14 in which said retaining-sealing member is carried on a set chamber.

20. The medical fluid set of claim 19 in which the sterility protector is integrally carried by a tube connector component.

21. The set of claim 14 in which said retaining-sealing member comprises a luer shape for sealingly receiving a luer connector.

22. A medical fluid set having a flow path which comprises: tubing sections interconnected with at least one tube connector component which connects said tubing sections together to form said set, said set further comprising external connectors carried on ends of at least some tubing sections of said set, at least one of said tube connector components comprising a connector positioned between different-diameter tubing sections of the set, said at least one tube connector component carrying, as an integral part thereof, a retaining-sealing member for removable, sealing connection with at least one of said external connectors, said retaining-sealing member being free of fluid flow connection with the set flow path.

23. A medical fluid set having a flow path which comprises: tubing sections interconnected with at least one tube connector component which connects said tubing sections together to form said set, said tube connector component comprising a set chamber, said set further comprising external connectors carried on ends of at least some tubing sections of said set, said set chamber carrying, as an integral part thereof, a retaining-sealing member for removable, sealing connection with at least one of said external connectors, said retaining-sealing member being free of fluid flow connection with the set flow path.

24. The set of claim 23 in which said retaining-sealing member comprises a luer-type connector having a closed end.

25. The set of claim 24 in which said luer-type connector is a male luer-type connector.

26. The medical fluid set of claim 23 in which said set chamber and said retaining-sealing member together comprise an integrally molded structure.

27. The medical fluid set of claim 26 in which said retaining-sealing member comprises a luer-type connector having a closed end.

28. A medical fluid set having a flow path which comprises: tubing sections interconnected with at least one tube connector component which connects said tubing sections together to form said set, said set further comprising external connectors carried on ends of at least some tubing sections of said set, at least one of said tube connector components or external connectors comprising an integrally molded structure with a retaining-sealing member for removable, sealing connection with at least one of said external connectors, said retaining-sealing member being free of fluid flow connection with the set flow path.

* * * * *